US00PP21159P2

(12) United States Plant Patent
Moreno et al.

(10) Patent No.: US PP21,159 P2
(45) Date of Patent: Jul. 13, 2010

(54) ***BUXUS* PLANT NAMED 'GREGEM'**

(50) Latin Name: *Buxus microphylla*
Varietal Denomination: Gregem

(75) Inventors: Rodrigo Moreno, El Campo, TX (US); Scott Maxwell, El Campo, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 12/386,470

(22) Filed: Apr. 17, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Penny J. Aguirre

(57) ABSTRACT

A new cultivar of *Buxus microphylla* 'Gregem', characterized by its small evergreen leaves, its dense compact growth habit, its vigorous growth rate, its hardiness to U.S.D.A Zone 5, and its ease of propagation by softwood cuttings.

2 Drawing Sheets

Botanical classification: *Buxus microphylla.*
Variety denomination: 'Gregem'.

BACKGROUND OF THE INVENTION

The present invention relates to a new and distinct cultivar of *Buxus microphylla* and will be referred to hereafter by its cultivar name, 'Gregem'. 'Gregem' is a new cultivar of boxwood grown for use as a container plant, hedging material and landscape shrub.

The new cultivar was discovered by one of the Inventors as a naturally occurring branch mutation of the cultivar 'Winter Gem' (not patented) growing in a container in a nursery in April 2000 in El Campo, Tex.

Asexual reproduction of the new cultivar was first accomplished by one of the Inventors using softwood stem cuttings in El Campo, Tex. in March 2002. The characteristics of 'Gregem' have been determined to be stable and are reproduced true to type in successive generations.

SUMMARY OF THE INVENTION

The following traits have been repeatedly observed and represent the characteristics of the new cultivar as grown outdoors in trial beds and in containers in El Campo, Tex. These attributes in combination distinguish 'Gregem' as a unique cultivar of *Buxus.*

1. 'Gregem' exhibits small, evergreen leaves.
2. 'Gregem' exhibits a compact, dense growth habit with leaves held very closely together.
3. 'Gregem' exhibits a vigorous growth rate.
4. 'Gregem' is readily propagated by softwood cuttings.
5. 'Gregem' is hardy to U.S.D.A Zone 5.

'Gregem' can be most closely compared to 'Winter Gem', the parent plant. In comparison to 'Winter Gem', 'Gregem' is similar to 'Winter Gem' in having a dwarf and compact growth habit, however 'Gregem' differs from 'Winter Gem' in having leaves that are smaller in size, in exhibiting a growth habit that is more dense, and in having a more vigorous growth rate. 'Gregem' may also be compared to 'Wintergreen' (not patented). Both cultivars have evergreen leaves, however 'Gregem' differs from 'Wintergreen' in having smaller leaves, a denser growth habit and by maturing to a smaller sized plant.

BRIEF DESCRIPTION OF THE DRAWING

The accompanying colored photographs illustrate the overall appearance and distinct characteristics of 3 year-old plants of the new *Buxus* as grown outdoors in three-gallon containers in El Campo, Tex.

The photograph in FIG. 1 is a side view and illustrates the overall plant habit and appearance of 'Gregem'.

Figure 1:
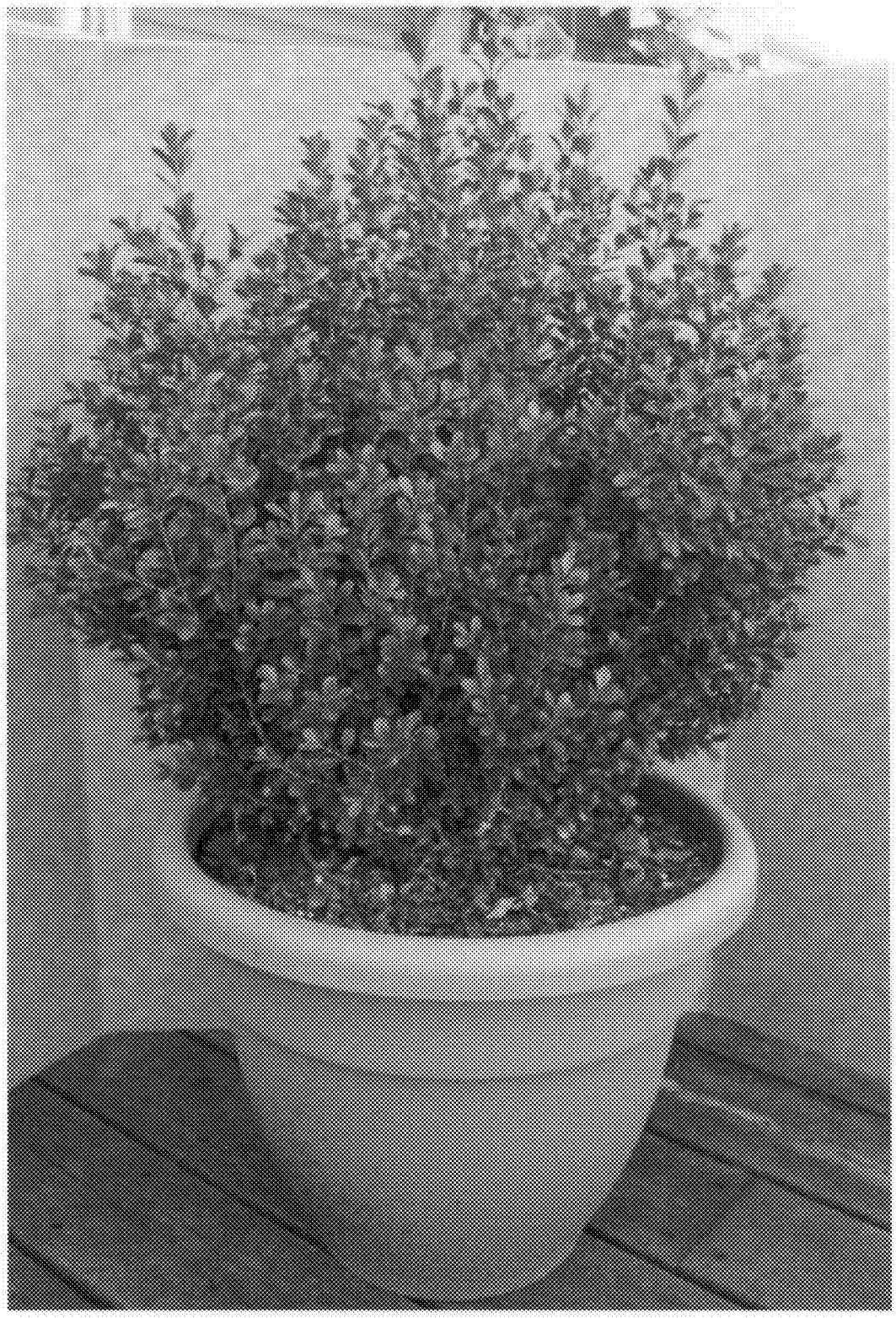
Figure 2:
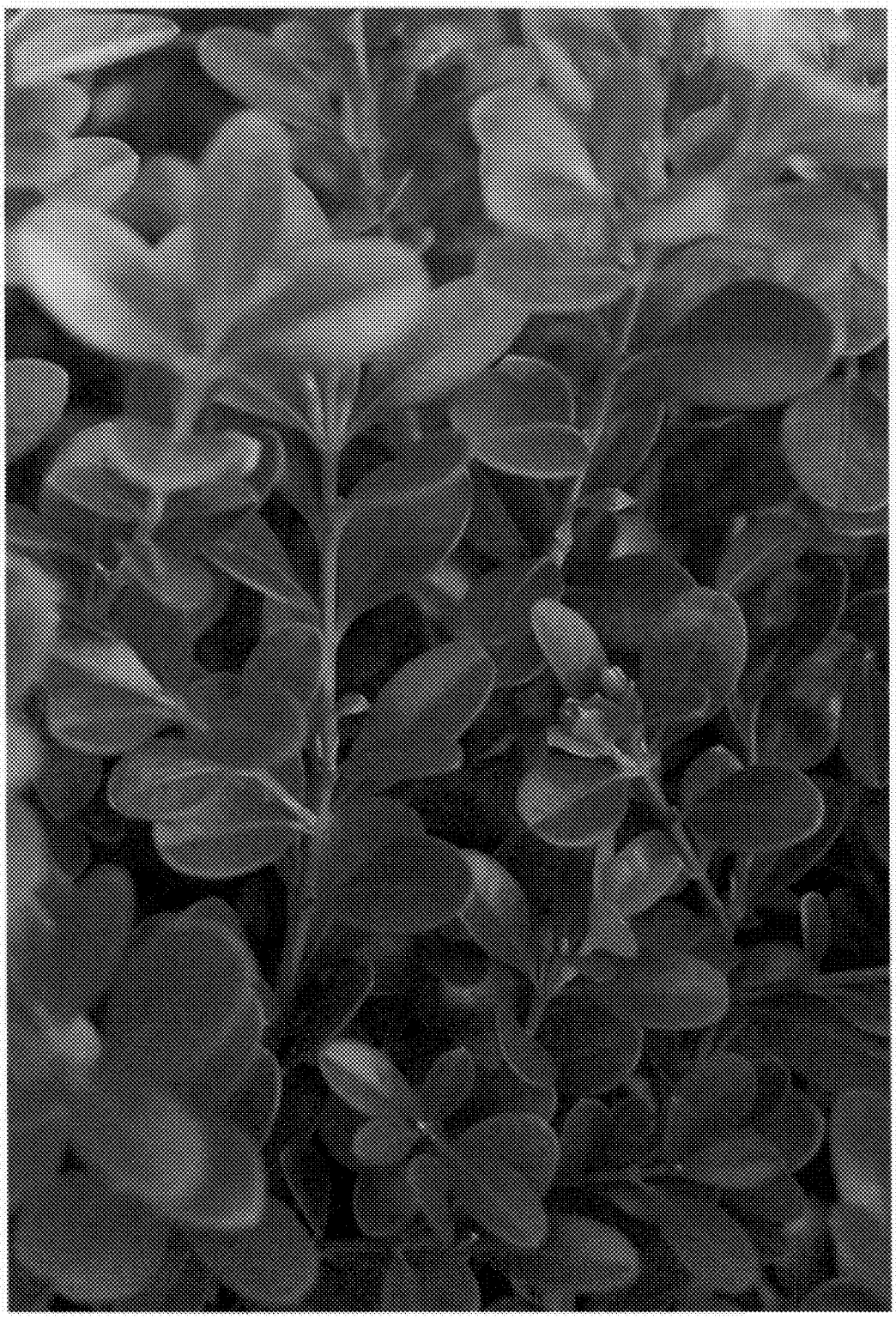

The photograph in FIG. 2 provides a close-up view of the foliage.

The colors in the photographs may differ slightly from the color values cited in the detailed botanical description, which accurately describe the colors of the new *Buxus*.

DETAILED BOTANICAL DESCRIPTION

The following is a detailed description of 3 year-old plants of the new cultivar as grown outdoors in three-gallon containers in El Campo, Tex. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Plant type.*—Evergreen, perennial shrub.

*Plant habit.*—Compact, dense, upright-mounded.

*Culture.*—Grows well in moist, fertile, well-drained soils and suitable for low maintenance plantings in sun to partial shade.

*Height and spread.*—Reaches about 60 cm in height and 50 cm in width.

*Cold hardiness.*—U.S.D.A. Zone 5.

*Diseases resistance.*—No susceptibility or resistance to diseases or pests has been observed.

*Root description.*—Fibrous.

Growth and propagation:

*Propagation.*—Softwood stem cuttings.

*Root development.*—Softwood stem cuttings callus in about 18 days, root initiation occurs in about 4 weeks at 25° C. under greenhouse conditions without supplemental lighting, cuttings are fully rooted in 10 to 12 weeks in a 24-cell tray without supplemental lighting.

*Growth rate.*—Vigorous relative to other boxwood cultivars.

Stem description:

*Shape.*—Quadrangular.

*Stem color.*—New growth emerges 144A lightly flushed with 165B, becoming 144A lightly flushed with 165A as it matures; mature wood has striations of 197B and 164D.

*Stem size.*—Lateral branches average about 33 cm in length and 2 mm in width.

*Stem surface.*—Lightly pubescent prior to bark formation.

*Internode length.*—Average of 2 cm between secondary branches and 1.2 cm between tertiary branches.

*Main branching.*—Stems arise from base, closely congested, average of 7 main branches, 7 lateral branches with tertiary branches dependant on pinching.

Foliage description:

*Leaf shape.*—Elliptic to obelliptic.

*Leaf division.*—Simple.

*Leaf base.*—Cuneate.

*Leaf apex.*—Rounded to retuse.

*Leaf fragrance.*—None.

*Leaf venation.*—Pinnate, midrib is conspicuous on lower surface only, 144A in color on upper surface, 144D in color on lower surface.

*Leaf margins.*—Entire.

*Leaf arrangement.*—Opposite.

*Leaf attachment.*—Sessile, sheathed on woody stems with sheathed portion about 3 mm in length and 2 mm in width.

*Leaf internode length.*—Average of 5 mm.

*Leaf surface.*—Glabrous and satiny on upper surface and glabrous and dull on lower surface, coreaceous in texture.

*Leaf size.*—Average of 1.8 cm in length and 1 cm in width when mature.

*Leaf quantity.*—Average of 21 on a branch 10 cm in length.

*Leaf color.*—Newly expanded leaves upper and lower surface; 144A, mature leaves upper surface; 139A, mature leaves lower surface; 137C.

*Stipels.*—About 1 mm in length, color 144A flushed with 165B at apex, pubescent.

*Stipules.*—Not present.

Inflorescence description: No flowers have been observed on the new cultivar to date.

It is claimed:

1. A new and distinct cultivar of *Buxus* plant named 'Gregem' as herein illustrated and described.

* * * * *